United States Patent
Hart et al.

(10) Patent No.: US 11,129,959 B2
(45) Date of Patent: Sep. 28, 2021

(54) INTRODUCER WITH EXPANDABLE CAPABILITIES

(71) Applicant: BOSTON SCIENTIFIC SCIMED, INC., Maple Grove, MN (US)

(72) Inventors: Matthew Hart, Maple Grove, MN (US); Corey N. Meyer, Zimmerman, MN (US); Derek Kenneth Larson, Golden Valley, MN (US); Benjamin Breidall, Eden Prairie, MN (US); Kevin Martin, Maple Grove, MN (US); Victoria Velez, Minneapolis, MN (US); Nathan Adams, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 134 days.

(21) Appl. No.: 16/276,971

(22) Filed: Feb. 15, 2019

(65) Prior Publication Data

US 2019/0247614 A1    Aug. 15, 2019

Related U.S. Application Data

(60) Provisional application No. 62/631,082, filed on Feb. 15, 2018.

(51) Int. Cl.
*A61M 25/00* (2006.01)
*A61M 25/06* (2006.01)
(Continued)

(52) U.S. Cl.
CPC ..... *A61M 25/0023* (2013.01); *A61B 17/3439* (2013.01); *A61B 90/39* (2016.02);
(Continued)

(58) Field of Classification Search
CPC .......... A61B 17/3439; A61M 25/0662; A61M 25/0029; A61M 25/0023;
(Continued)

(56) References Cited

U.S. PATENT DOCUMENTS

| 4,531,943 A | 7/1985 | Van Tassel et al. |
| 4,601,713 A | 7/1986 | Fuqua |

(Continued)

FOREIGN PATENT DOCUMENTS

| EP | 0103546 A1 | 3/1984 |
| EP | 0177177 A2 | 4/1986 |

(Continued)

OTHER PUBLICATIONS

International Search Report and Written Opinion dated May 10, 2019 for International Application No. PCT/US2019/018185.
(Continued)

*Primary Examiner* — Nathan R Price
*Assistant Examiner* — Tania Ismail
(74) *Attorney, Agent, or Firm* — Seager, Tufte & Wickhem LLP

(57) ABSTRACT

The present invention relates generally to medical devices and, in particular, to an introducer sheath that includes a shaft including a tubular portion, an expandable portion coupled to the tubular portion and a longitudinal axis. Additionally, the expandable portion includes a first pair of leaflets and a second pair of leaflets and both the first pair of leaflets and the second pair of leaflets extend along the longitudinal axis. Additionally, the second pair of leaflets are spaced radially inward of an inner surface of the first pair of leaflets and the expandable portion is designed to shift between a first configuration and a second radially expanded configuration.

17 Claims, 11 Drawing Sheets

(51) Int. Cl.
*A61B 17/34* (2006.01)
*A61B 90/00* (2016.01)

(52) U.S. Cl.
CPC ......... *A61M 25/0662* (2013.01); *A61B 90/03* (2016.02); *A61B 2090/3966* (2016.02); *A61M 25/0029* (2013.01); *A61M 25/0052* (2013.01); *A61M 2025/004* (2013.01); *A61M 2025/0024* (2013.01); *A61M 2025/0081* (2013.01); *A61M 2025/0681* (2013.01)

(58) Field of Classification Search
CPC .... A61M 2025/0024; A61M 2025/004; A61M 2025/0081
See application file for complete search history.

(56) References Cited

U.S. PATENT DOCUMENTS

| | | |
|---|---|---|
| 4,710,181 A | 12/1987 | Fuqua |
| 4,716,901 A | 1/1988 | Jackson et al. |
| 4,738,666 A | 4/1988 | Fuqua |
| 4,921,479 A | 5/1990 | Grayzel |
| 5,104,388 A | 4/1992 | Quackenbush |
| 5,158,545 A | 8/1992 | Trudell et al. |
| 5,176,659 A | 1/1993 | Mancini |
| 5,217,468 A | 6/1993 | Clement |
| 5,234,425 A | 8/1993 | Fogarty et al. |
| 5,256,150 A | 10/1993 | Quiachon et al. |
| 5,318,588 A | 6/1994 | Horzewski et al. |
| 5,320,611 A | 6/1994 | Bonutti et al. |
| 5,380,304 A | 1/1995 | Parker |
| 5,489,277 A | 2/1996 | Tolkoff et al. |
| 5,501,667 A | 3/1996 | Verdun |
| 5,514,091 A | 5/1996 | Yoon |
| 5,514,236 A | 5/1996 | Avellanet et al. |
| 5,674,240 A | 10/1997 | Bonutti et al. |
| 5,702,373 A | 12/1997 | Samson |
| 5,810,776 A | 9/1998 | Bacich et al. |
| 5,817,100 A | 10/1998 | Igaki |
| 5,827,227 A | 10/1998 | DeLago |
| 5,863,284 A | 1/1999 | Klein |
| 5,895,410 A | 4/1999 | Forber et al. |
| 5,964,730 A | 10/1999 | Williams et al. |
| 5,997,508 A | 12/1999 | Lunn et al. |
| 6,080,141 A | 6/2000 | Castro et al. |
| 6,090,072 A | 7/2000 | Kratoska et al. |
| 6,090,136 A | 7/2000 | McDonald et al. |
| 6,187,000 B1 | 2/2001 | Davison |
| 6,190,357 B1 | 2/2001 | Ferrari et al. |
| 6,197,016 B1 | 3/2001 | Fourkas et al. |
| 6,277,108 B1 | 8/2001 | Mcbroom et al. |
| 6,312,443 B1 | 11/2001 | Stone |
| 6,346,092 B1 | 2/2002 | Leschinsky |
| 6,358,238 B1 | 3/2002 | Sherry |
| 6,443,979 B1 | 9/2002 | Stalker |
| 6,494,860 B2 | 12/2002 | Rocamora et al. |
| 6,632,236 B2 | 10/2003 | Hogendijk |
| 6,652,492 B1 | 11/2003 | Bell et al. |
| 6,814,715 B2 | 11/2004 | Bonutti et al. |
| 6,899,727 B2 | 5/2005 | Armstrong et al. |
| 6,939,327 B2 | 9/2005 | Hall et al. |
| 7,144,386 B2 | 12/2006 | Korkor et al. |
| 7,226,451 B2 | 6/2007 | Shluzas et al. |
| 7,309,334 B2 | 12/2007 | Von Hoffman |
| 7,329,268 B2 | 2/2008 | Van Nguyen et al. |
| 7,438,712 B2 | 10/2008 | Chouinard |
| 7,534,250 B2 | 5/2009 | Schaeffer et al. |
| 7,591,832 B2 | 9/2009 | Eversull et al. |
| 7,655,016 B2 | 2/2010 | Demarais et al. |
| 7,665,016 B2 | 2/2010 | Behrens et al. |
| 7,670,354 B2 | 3/2010 | Davison et al. |
| 7,678,128 B2 | 3/2010 | Boyle et al. |
| 7,699,864 B2 | 4/2010 | Kick et al. |
| 7,713,193 B2 | 5/2010 | Nance et al. |
| 7,722,568 B2 | 5/2010 | Lenker et al. |
| 7,762,995 B2 | 7/2010 | Eversull et al. |
| 7,766,820 B2 | 8/2010 | Core |
| 7,780,692 B2 | 8/2010 | Nance et al. |
| 7,785,360 B2 | 8/2010 | Freitag |
| 7,785,630 B2 | 8/2010 | Freitag |
| 7,837,692 B2 | 11/2010 | Mulholland et al. |
| 7,837,769 B2 | 11/2010 | Lahr |
| 7,879,024 B2 | 2/2011 | Thortenson et al. |
| 7,892,203 B2 | 2/2011 | Lenker et al. |
| 7,927,309 B2 | 4/2011 | Palm |
| 7,951,110 B2 | 5/2011 | Bishop et al. |
| 7,963,952 B2 | 6/2011 | Wright, Jr. et al. |
| 8,034,072 B2 | 10/2011 | Nguyen et al. |
| 8,048,034 B2 | 11/2011 | Eversull et al. |
| 8,090,936 B2 | 1/2012 | Fallon et al. |
| 8,092,481 B2 | 1/2012 | Nance et al. |
| 8,252,015 B2 | 8/2012 | Leeflang et al. |
| 8,282,664 B2 | 10/2012 | Nance et al. |
| 8,317,817 B2 | 11/2012 | Davison et al. |
| 8,337,518 B2 | 12/2012 | Nance et al. |
| 8,414,645 B2 | 4/2013 | Dwork et al. |
| 8,562,559 B2 | 10/2013 | Bishop et al. |
| 8,562,673 B2 | 10/2013 | Yeung et al. |
| 8,597,277 B2 | 12/2013 | Lenker et al. |
| 8,652,203 B2 | 2/2014 | Quadri et al. |
| 8,668,668 B2 | 3/2014 | Bishop et al. |
| 8,690,936 B2 | 4/2014 | Nguyen et al. |
| 8,728,153 B2 | 5/2014 | Bishop et al. |
| 8,744,572 B1 | 6/2014 | Greenhut et al. |
| 8,764,704 B2 | 7/2014 | Lenker et al. |
| 8,790,387 B2 | 7/2014 | Nguyen et al. |
| 8,900,191 B2 | 12/2014 | Lenker et al. |
| 8,900,214 B2 | 12/2014 | Nance et al. |
| 9,044,577 B2 | 6/2015 | Bishop et al. |
| 9,089,669 B2 | 7/2015 | Haslinger et al. |
| 9,192,751 B2 | 11/2015 | Macaulay et al. |
| 9,192,752 B2 | 11/2015 | Leeflang et al. |
| 9,241,735 B2 | 1/2016 | Kick et al. |
| 9,254,374 B2 | 2/2016 | Thorstenson et al. |
| 9,259,813 B2 | 2/2016 | Heideman et al. |
| 9,301,840 B2 | 4/2016 | Nguyen et al. |
| 9,301,841 B2 | 4/2016 | Nguyen et al. |
| 9,320,508 B2 | 4/2016 | Carroux |
| 9,337,263 B2 | 5/2016 | Wu et al. |
| 9,387,314 B2 | 7/2016 | Bishop et al. |
| 9,393,041 B2 | 7/2016 | Barker et al. |
| 9,415,186 B2 | 8/2016 | Chebator et al. |
| 9,440,054 B2 | 9/2016 | Bishop et al. |
| 9,642,704 B2 | 5/2017 | Tuval et al. |
| 9,788,944 B2 | 10/2017 | Daly et al. |
| 9,801,619 B2 | 10/2017 | Lenker et al. |
| 9,801,657 B2 | 10/2017 | Furnish et al. |
| 9,907,931 B2 | 3/2018 | Birmingham et al. |
| 9,956,376 B2 | 5/2018 | Anderson et al. |
| 9,987,134 B2 | 6/2018 | Nguyen et al. |
| 10,327,896 B2 | 6/2019 | Zhou et al. |
| 10,391,279 B2 | 8/2019 | Zhou et al. |
| 10,391,280 B2 | 8/2019 | Zhou et al. |
| 10,391,281 B2 | 8/2019 | Zhou et al. |
| 2002/0032459 A1 | 3/2002 | Horzewski et al. |
| 2002/0123793 A1 | 9/2002 | Schaldach et al. |
| 2003/0004537 A1 | 1/2003 | Boyle et al. |
| 2004/0006344 A1 | 1/2004 | Nguyen et al. |
| 2004/0087968 A1 | 5/2004 | Core |
| 2004/0122415 A1 | 6/2004 | Johnson |
| 2005/0080430 A1 | 4/2005 | Wright, Jr. et al. |
| 2005/0085842 A1 | 4/2005 | Eversull et al. |
| 2005/0124937 A1 | 6/2005 | Kick et al. |
| 2005/0125021 A1 | 6/2005 | Nance et al. |
| 2005/0216047 A1 | 9/2005 | Kumoyama et al. |
| 2005/0222576 A1 | 10/2005 | Kick et al. |
| 2006/0020321 A1 | 1/2006 | Parker |
| 2006/0135962 A1 | 6/2006 | Kick et al. |
| 2006/0135981 A1 | 6/2006 | Lenker et al. |
| 2006/0217755 A1 | 9/2006 | Eversull et al. |
| 2007/0021768 A1 | 1/2007 | Nance et al. |
| 2007/0074805 A1 | 4/2007 | Leeflang et al. |
| 2007/0087148 A1 | 4/2007 | Okushi et al. |
| 2008/0004521 A1 | 1/2008 | Hundley et al. |

(56) References Cited

U.S. PATENT DOCUMENTS

| | | |
|---|---|---|
| 2008/0004571 A1 | 1/2008 | Voss |
| 2008/0114331 A1 | 5/2008 | Holman et al. |
| 2008/0200943 A1 | 8/2008 | Barker et al. |
| 2008/0243081 A1 | 10/2008 | Nance et al. |
| 2009/0043285 A1 | 2/2009 | Stehr et al. |
| 2009/0287182 A1 | 11/2009 | Bishop et al. |
| 2010/0049313 A1 | 2/2010 | Alon et al. |
| 2010/0094209 A1 | 4/2010 | Drasler et al. |
| 2010/0094392 A1 | 4/2010 | Nguyen et al. |
| 2010/0198160 A1 | 8/2010 | Voss |
| 2011/0112567 A1 | 5/2011 | Lenker et al. |
| 2011/0190697 A1 | 8/2011 | Farnan |
| 2011/0251681 A1 | 10/2011 | Shipley et al. |
| 2012/0116439 A1 | 5/2012 | Ho |
| 2012/0158033 A1 | 6/2012 | Deal et al. |
| 2012/0323180 A1 | 12/2012 | Chebator et al. |
| 2013/0030369 A1 | 1/2013 | Root et al. |
| 2013/0079861 A1 | 3/2013 | Reinert et al. |
| 2013/0131718 A1 | 5/2013 | Jenson et al. |
| 2013/0178711 A1 | 7/2013 | Avneri et al. |
| 2013/0231735 A1 | 9/2013 | Deem et al. |
| 2013/0281787 A1 | 10/2013 | Avneri et al. |
| 2014/0121629 A1 | 5/2014 | Macaulay et al. |
| 2014/0236122 A1 | 8/2014 | Anderson et al. |
| 2014/0236123 A1 | 8/2014 | Birmingham et al. |
| 2014/0379067 A1 | 12/2014 | Nguyen et al. |
| 2015/0073333 A1 | 3/2015 | Knowles |
| 2015/0182723 A1 | 7/2015 | Leeflang et al. |
| 2015/0238178 A1 | 8/2015 | Carroux |
| 2015/0265798 A1 | 9/2015 | Nihonmatsu et al. |
| 2015/0320971 A1 | 11/2015 | Leeflang et al. |
| 2016/0074067 A1 | 3/2016 | Furnish et al. |
| 2016/0135840 A1 | 5/2016 | Kick et al. |
| 2016/0213882 A1 | 7/2016 | Fitterer et al. |
| 2016/0296332 A1 | 10/2016 | Zhou et al. |
| 2016/0296730 A1 | 10/2016 | Zhou et al. |
| 2017/0014156 A1 | 1/2017 | Steffen |
| 2017/0014157 A1 | 1/2017 | Coyle et al. |
| 2017/0072163 A1 | 3/2017 | Lim et al. |
| 2017/0209133 A1 | 7/2017 | Ciulla et al. |
| 2017/0245864 A1 | 8/2017 | Franano et al. |
| 2017/0252062 A1 | 9/2017 | Fitterer et al. |
| 2018/0161064 A1 | 6/2018 | Fitterer et al. |
| 2018/0199960 A1 | 7/2018 | Anderson et al. |
| 2018/0221149 A1 | 8/2018 | Reynolds et al. |
| 2018/0229000 A1 | 8/2018 | Anderson et al. |
| 2018/0325548 A1 | 11/2018 | Haverkost et al. |
| 2018/0325549 A1 | 11/2018 | Thoreson et al. |
| 2019/0021834 A1 | 1/2019 | Nir et al. |
| 2019/0029820 A1 | 1/2019 | Zhou et al. |
| 2019/0029822 A1 | 1/2019 | Nguyen et al. |
| 2019/0029823 A1 | 1/2019 | Nguyen et al. |
| 2019/0029824 A1 | 1/2019 | Nguyen et al. |
| 2019/0029825 A1 | 1/2019 | Fitterer et al. |
| 2019/0030298 A1 | 1/2019 | Zhou et al. |
| 2019/0030299 A1 | 1/2019 | Zhou et al. |

FOREIGN PATENT DOCUMENTS

| | | |
|---|---|---|
| EP | 0249456 A2 | 12/1987 |
| EP | 0385920 A2 | 9/1990 |
| EP | 0592410 A1 | 4/1994 |
| EP | 1139889 B1 | 4/2006 |
| EP | 1660167 A2 | 5/2006 |
| EP | 1793881 A2 | 6/2007 |
| EP | 1804860 B1 | 4/2014 |
| EP | 2288403 B1 | 11/2014 |
| EP | 2862590 A1 | 4/2015 |
| EP | 2911729 A1 | 9/2015 |
| EP | 1694398 B1 | 3/2016 |
| EP | 2101661 B1 | 3/2016 |
| EP | 2995268 A1 | 3/2016 |
| EP | 2475417 B1 | 10/2018 |
| JP | 2012040145 A | 3/2012 |
| WO | 9219312 A1 | 11/1992 |
| WO | 9307812 A1 | 4/1993 |
| WO | 9829026 A2 | 7/1998 |
| WO | 2003002181 A2 | 1/2003 |
| WO | 2004002562 A2 | 1/2004 |
| WO | 2004037333 A1 | 5/2004 |
| WO | 2006069215 A2 | 6/2006 |
| WO | 2007035471 A2 | 3/2007 |
| WO | 2008002915 A2 | 1/2008 |
| WO | 2008042311 A1 | 4/2008 |
| WO | 2008147964 A1 | 12/2008 |
| WO | 2009035745 A1 | 3/2009 |
| WO | 2013044942 A1 | 4/2013 |
| WO | 2014140093 A1 | 9/2014 |
| WO | 2018148488 A1 | 8/2018 |

OTHER PUBLICATIONS

International Search Report and Written Opinion PCT/US2016/016608, 11 pages, dated Apr. 21, 2016.
International Search Report and Written Opinion PCT/2016/014401, 19 pages, dated Jul. 12, 2016.
International Search Report and Written Opinion dated May 15, 2017 for International Application No. PCT/US2017/020010.
510K Premarket Notification, Jun. 22, 2018. https://www.accessdata.fda.gov/scripts/cdrh/cfdocs/cfpmn/pmn.cfm?ID=K181051.
BSX Structural Heart Update 2018, Feb. 2018.
International Search Report and Written Opinion dated May 28, 2018 for International Application No. PCT/US2018/017539.

INTRODUCER WITH EXPANDABLE CAPABILITIES

CROSS-REFERENCE TO RELATED APPLICATIONS

This application claims the benefit of priority under 35 U.S.C. § 119 to U.S. Provisional Application Ser. No. 62/631,082, filed Feb. 15, 2018, the entirety of which is incorporated herein by reference.

TECHNICAL FIELD

The disclosure relates generally to medical devices and more particularly to medical devices that are adapted for use in percutaneous medical procedures.

BACKGROUND

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilize to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough).

SUMMARY

This disclosure provides design, material, manufacturing method, and use alternatives for medical devices. An example introducer sheath includes a shaft including a tubular portion, an expandable portion coupled to the tubular portion and a longitudinal axis. Additionally, the expandable portion includes a first pair of leaflets and a second pair of leaflets and both the first pair of leaflets and the second pair of leaflets extend along the longitudinal axis. Additionally, the second pair of leaflets are spaced radially inward of an inner surface of the first pair of leaflets and the expandable portion is designed to shift between a first configuration and a second expanded configuration.

Alternatively or additionally to any of the examples above, wherein the first pair of leaflets includes a first leaflet and a second leaflet, wherein the first leaflet includes a first concave surface extending partially around the longitudinal axis, where the second leaflet includes a second concave surface extending partially around the longitudinal axis and wherein the first concave surface faces the second concave surface.

Alternatively or additionally to any of the examples above, wherein the second pair of leaflets includes a third leaflet and a fourth leaflet, wherein the third leaflet includes a third concave surface extending partially around the longitudinal axis, where the fourth leaflet includes a fourth concave surface extending partially around the longitudinal axis and wherein the third concave surface faces the fourth concave surface.

Alternatively or additionally to any of the examples above, wherein the first pair of leaflets are circumferentially offset from the second pair of leaflets.

Alternatively or additionally to any of the examples above, wherein the first leaflet is spaced away from the second leaflet to form a first gap extending along the longitudinal axis and a second gap extending along the longitudinal axis.

Alternatively or additionally to any of the examples above, wherein the third leaflet is spaced away from the fourth leaflet to form a third gap extending along the longitudinal axis and a fourth gap extending along the longitudinal axis.

Alternatively or additionally to any of the examples above, wherein the first leaflet and the second leaflet are configured to flex radially outward and away from one another when the expandable portion shifts from the first configuration to the second expanded configuration.

Alternatively or additionally to any of the examples above, wherein the third leaflet and the fourth leaflet are configured to flex radially outward and away from one another when the expandable portion shifts from the first configuration to the second expanded configuration.

Alternatively or additionally to any of the examples above, wherein the first and second leaflets include an inner surface and wherein the third and fourth leaflets include an outer surface, and wherein the outer surface of the third and fourth leaflets are configured to slide along the inner surfaces of the first and second leaflets when the expandable portion shifts from the first configuration to the second expanded configuration.

Alternatively or additionally to any of the examples above, wherein the third leaflet includes an outer surface and a first rib member disposed along the outer surface, and wherein the fourth leaflet includes an outer surface and a second rib member disposed along the outer surface.

Alternatively or additionally to any of the examples above, wherein the first rib member is positioned within the first gap and wherein the second rib member is positioned within the second gap.

Alternatively or additionally to any of the examples above, wherein the first leaflet includes a first projection extending radially inward from an inner surface of the first leaflet, and wherein the third leaflet includes a second projection extending radially outward from an outer surface of the third leaflet, and wherein the first projection is configured to engage the second projection.

Alternatively or additionally to any of the examples above, wherein the engagement of the first projection with the second projection is configured to limit the radial expansion of the expandable portion.

Another example introducer includes:
a hub; and
a shaft including a tubular member and an expandable portion coupled to a distal end region of the tubular member, and wherein a proximal end region of the tubular member is coupled to a distal portion of the hub;
wherein the tubular member has a constant outer diameter from the distal end region to the proximal end region;
wherein the expandable portion includes a first pair of leaflets and a second pair of leaflets spaced around a longitudinal axis of the expandable portion;
wherein the second pair of leaflets are spaced radially inward of an inner surface of the first pair of leaflets.

Alternatively or additionally to any of the examples above, wherein the expandable portion is designed to shift between a first configuration and a second expanded configuration.

Alternatively or additionally to any of the examples above, wherein the first pair of leaflets includes a first leaflet and a second leaflet, wherein the first leaflet includes a first concave surface extending around the longitudinal axis, where the second leaflet includes a second concave surface extending around the longitudinal axis and wherein the first concave surface faces the second concave surface.

Alternatively or additionally to any of the examples above, wherein the second pair of leaflets includes a third leaflet and a fourth leaflet, wherein the third leaflet includes a third concave surface extending around the longitudinal axis, where the fourth leaflet includes a fourth concave surface extending around the longitudinal axis and wherein the third concave surface faces the fourth concave surface.

Alternatively or additionally to any of the examples above, wherein the first pair of leaflets is circumferentially offset from the second pair of leaflets.

Alternatively or additionally to any of the examples above, wherein the first leaflet, the second leaflet, the third leaflet and the fourth leaflet are configured to expand radially outward and away from one another when the expandable portion shifts from the first configuration to the second expanded configuration.

Another example introducer sheath includes:

a shaft including a tubular portion and an expandable portion coupled to the tubular portion;

wherein the expandable portion includes a first leaflet, a second leaflet, a third leaflet and a fourth leaflet spaced around the longitudinal axis of the expandable member;

wherein the first leaflet, the second leaflet, the third leaflet and the fourth leaflet are circumferentially offset from one another around the longitudinal axis; and wherein the expandable portion is designed to shift between a first configuration and a second expanded configurations.

The above summary of some examples is not intended to describe each disclosed embodiment or every implementation of the present disclosure. The Figures, and Detailed Description, which follow, more particularly exemplify these examples.

Figure 1:
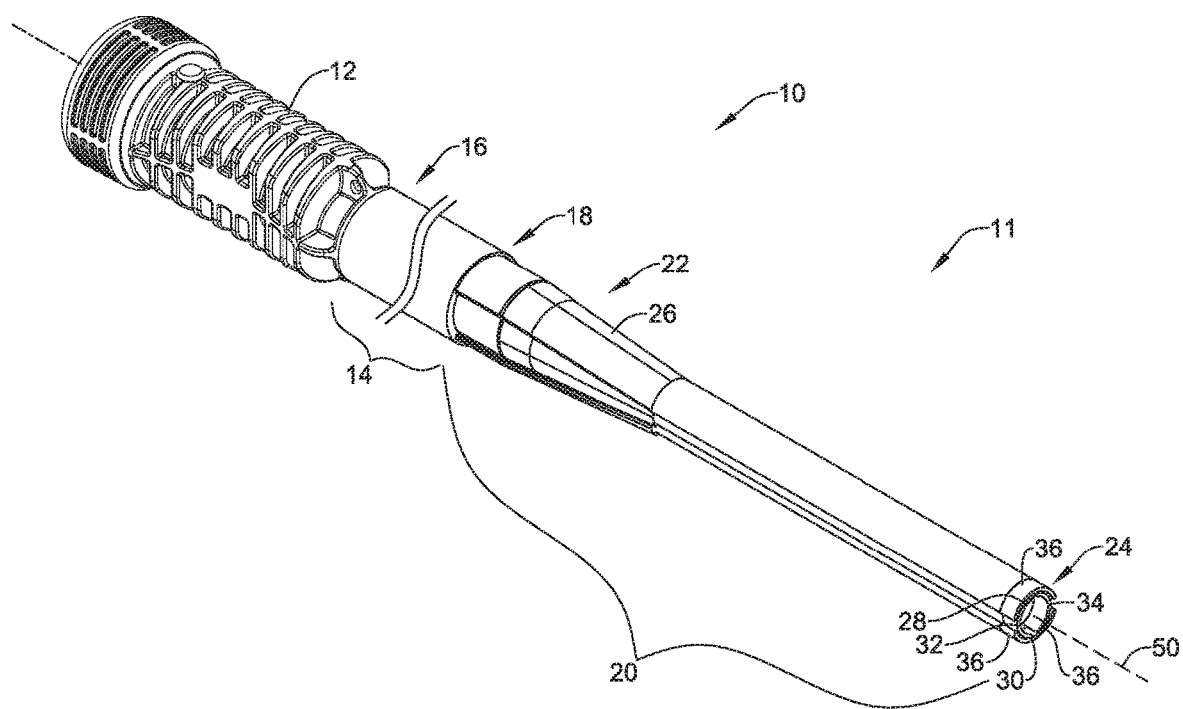
FIG. 1 is a perspective view of an example introducer.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some examples", "other examples", etc., indicate that the embodiment described may include one or more particular features, structures, and/or characteristics. However, such recitations do not necessarily mean that all examples include the particular features, structures, and/or characteristics. Additionally, when particular features, structures, and/or characteristics are described in connection with one embodiment, it should be understood that such features, structures, and/or characteristics may also be used connection with other examples whether or not explicitly described unless clearly stated to the contrary.

The following detailed description should be read with reference to the drawings in which similar elements in different drawings are numbered the same. The drawings, which are not necessarily to scale, depict illustrative examples and are not intended to limit the scope of the disclosure.

In some instances, performing percutaneous medical procedures may require the insertion and/or maneuvering of relatively large medical devices through a patient's vasculature. However, inserting the medical device into the vasculature may result in undesirable forces being applied to the vessel walls. For example, as the medical device passes into the vasculature, it may make undesirable contact with one or more vessel walls. This interference may cause injury to the vessel as the medical device is navigated into calcified or diseased vessels. Therefore, in some instances an introducer is utilize to facilitate the insertion of medical devices into the vessel. Further, vessel trauma resulting from forces applied to the vessel wall by a medical device may be lessened by minimizing the size of an introducer used to access the vessel. Therefore, it may be desirable to design an introducer having a reduced insertion profile, yet capable of expansion when necessary (e.g., during the passage of a medical device therethrough). The following examples disclose an intravascular medical device including an expandable introducer, whereby the introducer is designed to expand from a reduced profile, unexpanded configuration to an expanded configuration.

FIG. 1 illustrates an example expandable introducer (e.g., delivery sheath, access sheath, etc.) 10. The introducer 10 may include a hub 12 and a shaft 11. The shaft 11 may include a tubular member 14 and an expandable portion 20. The tubular member 14 may include a proximal end region 16 and a distal end region 18. Further, the proximal end region 16 of the tubular member may be attached to a distal end of the hub member 12. Both the hub 12 and the tubular member 14 may include a lumen extending therethrough. The lumen extending through the hub 12 and the tubular member 14 (along with expandable portion 20) may be designed to permit a medical device to pass from outside a patient's body, through the introducer 10 to a location inside the patient's body.

The hub 12 may include a hemostatic valve or seal disposed therein. The hemostatic valve or seal may prevent blood or other bodily fluid(s) from flowing proximally through the lumen of the tubular member 14. In at least some examples, the hub 12 may include a port in fluid communication with the lumen of the tubular member 14.

The expandable portion 20 of the introducer 10 may include a proximal end region 22 and a distal end region 24. Additionally, the proximal end region 22 of the expandable portion 20 may include a tapered region 26. In some examples, the tapered region 26 may be positioned distal to the distal end region 18 of the tubular member 14. In some examples at least a portion of the expandable portion 20 may have a substantially constant outer diameter which transitions into tapered portion 26. At least a portion of tapered portion 26 may have an outer diameter which is greater than the outer diameter of at least a portion of expandable portion 20 which is distal to the tapered portion 26. However, this is not intended to be limiting. It is contemplated that any portion of the introducer 10 may include any number of tapers, constant diameter regions or combinations thereof.

FIG. 1 further illustrates that introducer 10 may include one or more overlapping leaflets extending along the longitudinal axis 50 of the introducer 10. For example, FIG. 1 shows a first leaflet 28, a second leaflet 30, a third leaflet 32 and a fourth leaflet 34 positioned around the longitudinal axis 50 of the introducer 10. However, this is not intended to be limiting. For example, it is contemplated that the introducer 10 may include 1, 2, 3, 4, 5, 6 or more leaflets.

FIG. 1 further illustrates that each of the first leaflet 28, the second leaflet 30, the third leaflet 32 and the fourth leaflet 34 may extend from the distal end region 24 of the expandable portion 20 to the proximal end region 22 of the expandable portion. Further, the proximal ends of each of the first leaflet 28, the second leaflet 30, the third leaflet 32 and the fourth leaflet 34 may be attached to the distal end region 18 of the tubular member 14. Additionally, FIG. 1 illustrates that each of the first leaflet 28, the second leaflet 30, the third leaflet 32 and the fourth leaflet 34 may include a tapered region. However, this is not intended to be limiting. Rather, it is contemplated that none of the first leaflet 28, the second leaflet 30, the third leaflet 32 and the fourth leaflet 34 may include a tapered portion. However, in other examples any combination of the first leaflet 28, the second leaflet 30, the third leaflet 32 and the fourth leaflet 34 may include a tapered portion.

Further, while FIG. 1 illustrates that the length of the first leaflet 28, the second leaflet 30, the third leaflet 32 and the fourth leaflet 34 (as measured along the longitudinal axis 50) is substantially equivalent, it is contemplated that, in some examples, any of the first leaflet 28, the second leaflet 30, the third leaflet 32 and the fourth leaflet 34 may have variable lengths as measured along the longitudinal axis 50.

In some examples it may be desirable to add a tip member to the distal end of any of the example introducers disclosed herein. FIG. 1 shows an example tip member 36 disposed along each of the first leaflet 28, the second leaflet 30, the third leaflet 32 and the fourth leaflet 34. The tip members 36 may be designed with a low durometer material. In some instances, a lower durometer material may provide the tip members 36 with the ability to radially expand (e.g., flex) outward and radially contract as a variety of medical devices are advanced through the tip members 36. Further, the tip members 36 may include a taper. For example, the tip members 36 may taper from a first diameter to a second diameter at the distal end of introducer 10. While not intended to be limiting, in some examples the shape of the tip members 36 (in combination with one another) may resemble a bull-nose. Additionally, one or more of the tip members 36 may include a radiopaque material. The radiopaque material may allow the tip members 36 to be visualized by a clinician during a medical procedure. Additionally, while not illustrated in FIG. 1, it can be appreciated that a tip member 36 may be included on any combination of the first leaflet 28, the second leaflet 30, the third leaflet 32 and/or the fourth leaflet 34. In other words, in some examples the tip member 36 may not be included on all the individual leaflets.

Figure 2:
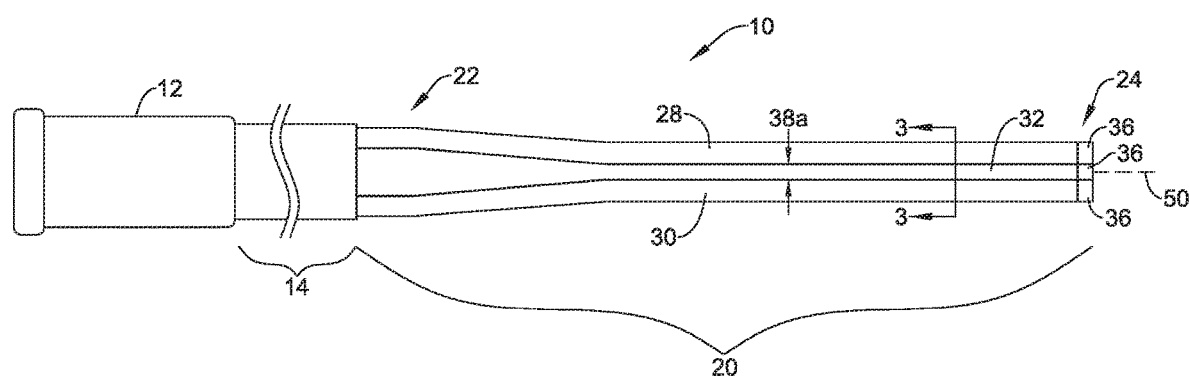
FIG. 2 is a side view of the example introducer of FIG. 1.

FIG. 2 illustrates a side view of the introducer 10 shown in FIG. 1. As discussed above, FIG. 2 shows the first leaflet 28, the second leaflet 30 and the third leaflet 32 extending from the proximal end region 22 to the distal end region 24 (note that the fourth leaflet 34 extends from the proximal end region 22 to the distal end region 24, but is hidden from view in FIG. 2 by the third leaflet 32). Additionally, FIG. 2 shows the tip members 36 disposed along the distal ends of the first leaflet 28, the second leaflet 30 and the third leaflet 32. As will be discussed in greater detail below, FIG. 2 illustrates that, in some examples, the first leaflet 28 may be spaced away from the second leaflet 30 to define a first gap 38a between the first leaflet 28 and the second leaflet 30. It can be appreciated that the first gap 38a may extend along the longitudinal axis 50 from the proximal end region 22 to the distal end region 24 of the expandable member 20.

Figure 3:
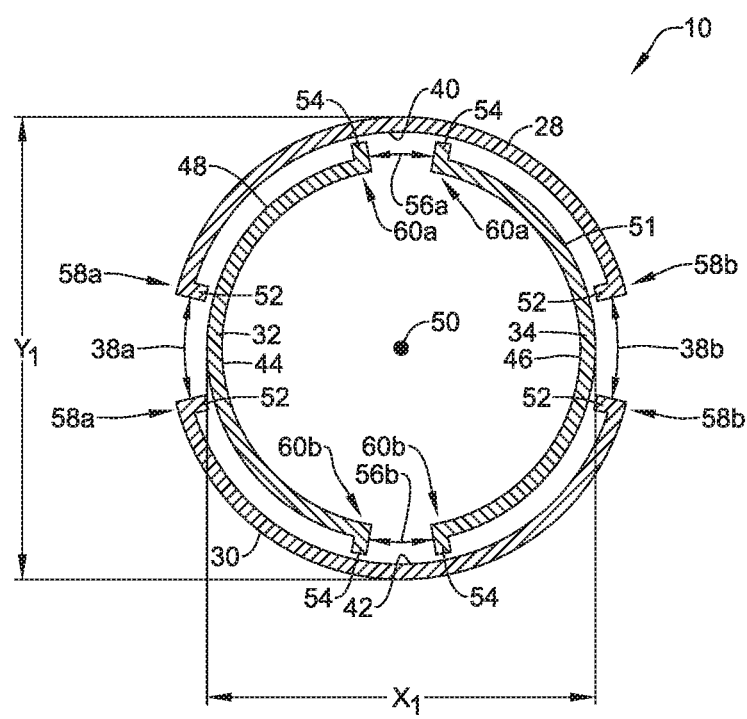
FIG. 3 is a cross-sectional view taken along line 3-3 of FIG. 2.

FIG. 3 is a cross-sectional view of the introducer 10 taken along line 3-3 of FIG. 2. As will be described in greater detail below, FIG. 3 represents a cross-section of expandable portion 20 in an unexpanded configuration.

As described above, FIG. 3 shows the first leaflet 28, the second leaflet 30, the third leaflet 32 and the fourth leaflet 34 circumferentially spaced around the longitudinal axis 50 of the introducer 10. As shown in FIG. 3, the first leaflet 28, the second leaflet 30, the third leaflet 32 and the fourth leaflet 34 may overlap and yet be circumferentially offset from one another around the longitudinal axis 50. In some instances, the first leaflet 28, the second leaflet 30, the third leaflet 32 and the fourth leaflet 34 may be offset substantially equidistant from one another. In other words, the degree for which each of the first leaflet 28, the second leaflet 30, the third leaflet 32 and the fourth leaflet 34 are circumferentially offset from one another may be substantially equivalent between individual leaflets. However, it is further contemplated that the leaflets may be spaced at variable distances around the longitudinal axis 50.

Additionally, it can be appreciated that, in some examples, the first leaflet 28 and the second leaflet 30 may define a first "pair" of leaflets, while the third leaflet 32 and the fourth leaflet 34 may define a second "pair" of leaflets. It can further be appreciated that the first pair of leaflets (e.g., the first leaflet 28 and the second leaflet 30) may be circumferentially offset from the second pair of leaflets (e.g., the third leaflet 32 and the second leaflet 34).

FIG. 3 further illustrates that the first leaflet 28 may include an inner surface 40 and the second leaflet 30 may include an inner surface 42. Further, each of the inner surface 40 and the inner surface 42 may be concave surfaces with respect to the central longitudinal axis 50. Additionally, the inner concave surface 40 and the inner concave surface 42 may face one another.

FIG. 3 further illustrates that the third leaflet 32 may include an inner surface 44 and the fourth leaflet 34 may include an inner surface 46. Further, each of the inner surface 44 and the inner surface 46 may be concave surfaces with respect to the central longitudinal axis 50. Additionally, the inner concave surface 44 and the inner concave surface 46 may face one another.

As shown in FIG. 3, the outer surfaces of the first leaflet 28 and the second leaflet 30 (in combination) may define an outer extent depicted as "$Y_1$" while the outer surfaces of the third leaflet 32 and the fourth leaflet 34 (in combination) may include an outer extent depicted as "$X_1$." It can be appreciated from FIG. 3 that the extent "$Y_1$" may be greater than the extent "$X_1$." In other words, the third leaflet 32 and the fourth leaflet 34 (in combination) may be positioned radially inward of the first leaflet 28 and the second leaflet 30 (in combination).

As discussed above, FIG. 3 illustrates that the first leaflet 28 may be spaced away from the second leaflet 30 to define a first gap 38a (shown above with respect to FIG. 2) and a second gap 38b. Similarly, FIG. 3 illustrates that the third leaflet 32 may be spaced away from the fourth leaflet 34 to define a third gap 56a and a fourth gap 56b. It can be appreciated that the first gap 38a, the second gap 38b, the third gap 56a and the fourth gap 56b may extend along the longitudinal axis 50 from the distal end region to the proximal end region of the expandable member 20.

Additionally, FIG. 3 illustrates that the first leaflet 28 and the second leaflet 30 may include one or more projections 52 extending radially inward from the inner surface 40 of the first leaflet 28 and/or from the inner surface 42 of the second leaflet 30. For example, each of the first leaflet 28 and the second leaflet 30 may include a projection 52 positioned adjacent to a first lateral edge 58a and or a second lateral edge 58b. Similarly, the third leaflet 32 and the fourth leaflet 34 may include one or more projections 54 extending radially outward from the outer surface 48 of the third leaflet 32 and/or from the outer surface 51 of the fourth leaflet 34. For example, each of the third leaflet 32 and the fourth leaflet 34 may include a projection 54 positioned adjacent to a first lateral edge 60a and or a second lateral edge 60b. As will be described in greater detail below, the projections 52 extending radially inward from the first leaflet 28 and/or the second leaflet 30 may engage with the projections 54 extending radially outward from the third leaflet 32 and/or the fourth leaflet 34.

As discussed above, in some examples it may be desirable to design introducer 10 to permit a medical device (e.g., heart valve) to pass therethrough. For example, it may be desirable to permit a medical device to pass through hub 12, tubular member 14 and the expandable portion 20 (for example, to pass through introducer 10 while being inserted into a body lumen). Further, in some instances it may be desirable to design introducer 10 to radially expand such that it can accommodate devices which have an outer diameter greater than the unexpanded inner diameters of hub 12, tubular member 14 and the expandable portion 20.

Figure 4:
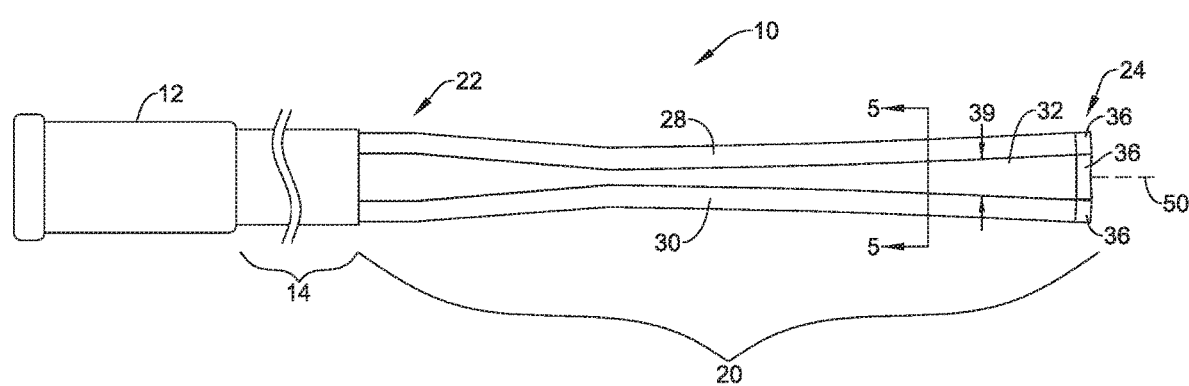
FIG. 4 is a side view of the introducer of FIG. 1 in an expanded configuration.
Figure 5:
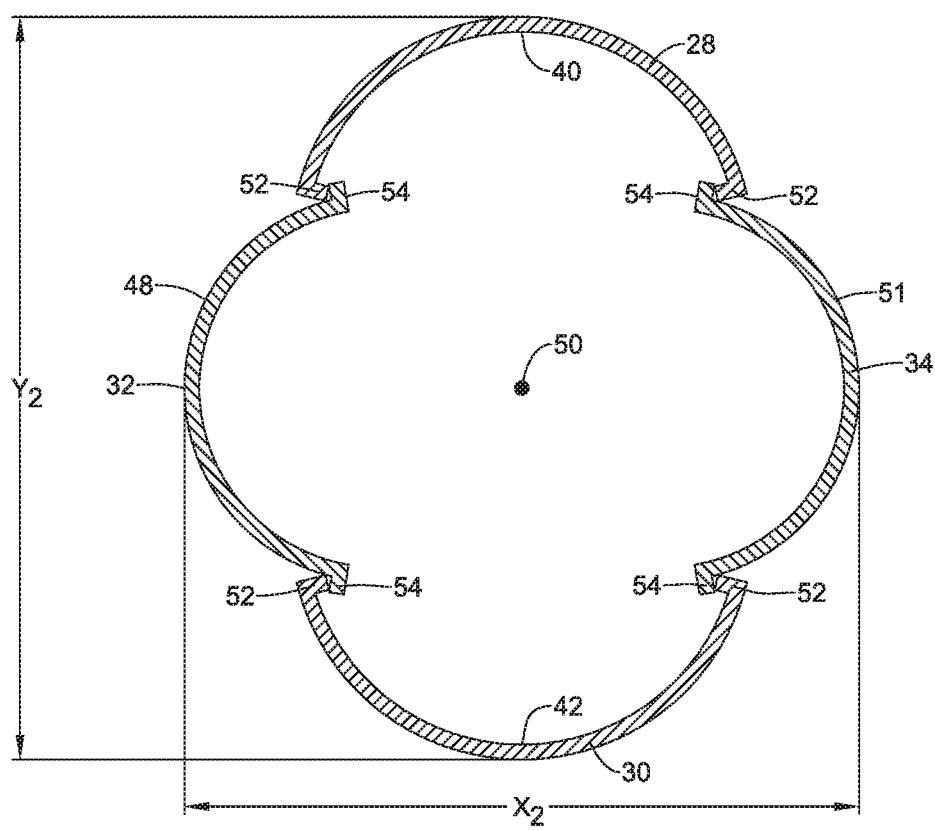
FIG. 5 is a cross-sectional view taken along line 5-5 of FIG. 4.

FIG. 4 and FIG. 5 represent the expandable portion 20 of the introducer 10 in an example expanded configuration. In particular, FIG. 4 illustrates an example configuration of the expandable portion 20 shown in FIG. 2 after the introducer 10 has been expanded radially outward. Further, FIG. 5 may represent the cross-section of the expandable member 20 shown in FIG. 4 (e.g., introducer 10 after it has been expanded radially outward). In other words, the expandable portion 20 of the introducer 10 may shift between a first configuration and a second configuration, whereby the first configuration may represent an unexpanded configuration (illustrated in FIGS. 1-3) while the second configuration (illustrated in FIGS. 4-5) may represent an expanded configuration.

FIG. 4 shows the introducer 10 described above including the hub member 12, the tubular member 14 and the expandable portion 20. FIG. 4 illustrates the tip members 36 disposed along the distal end of the expandable portion 20. Further, FIG. 4 illustrates that in the expanded configuration, the first leaflet 28 and the second leaflet 30 may flex radially away from the longitudinal axis 50. In other words, both the first leaflet 28 and the second leaflet 30 may flex away from one another, thereby increasing the gap 38a (shown in FIG. 2 and FIG. 3) to an expanded gap 39. As will be described in greater detail in FIG. 5, the third leaflet 32 and the fourth leaflet 34 may also flex radially away from the longitudinal axis 50, however, this is not shown in FIG. 4 as the third leaflet 32 and fourth leaflet 34 are flexing out and into the page, respectively. It can be appreciated that the ability of the first leaflet 28, the second leaflet 30, the third leaflet 32 and the fourth leaflet 34 to flex radially away from the longitudinal axis 50 may permit a medical device to pass through the introducer 10.

As discussed above, FIG. 5 illustrates a cross-sectional view of the introducer 10 taken along line 5-5 of FIG. 4. FIG. 5 shows the first leaflet 28, the second leaflet 30, the third leaflet 32 and the fourth leaflet 34 flexed radially away from the longitudinal axis 50. As shown in FIG. 5, the first leaflet 28 and the second leaflet 30 may define an outer extent depicted as "$Y_2$." It can be appreciated that the expanded outer extent $Y_2$ may be greater than the unexpanded extent $Y_1$ shown in FIG. 3. Further, the third leaflet 32 and the fourth leaflet 34 may define an outer extent depicted as "$X_2$." It can be appreciated that the expanded outer extent $X_2$ may be greater than the unexpanded outer extent $X_1$ shown in FIG. 3.

FIG. 4 illustrates the first leaflet 28, the second leaflet 30, the third leaflet 32 and the fourth leaflet 34 flexed radially away from the longitudinal axis 50 such that the distal end region 24 of introducer may be substantially "cone-shaped." However, this is not intended to be limiting. Rather, in other examples, it is contemplated that the first leaflet 28, the second leaflet 30, the third leaflet 32 and the fourth leaflet 34 may expand radially away from the longitudinal axis 50 such that each of the first leaflet 28, the second leaflet 30, the third leaflet 32 and the fourth leaflet 34 remain substantially parallel to one another along the longitudinal axis 50 while shifting between an unexpanded configuration and an expanded configuration. In yet other examples, it is contemplated that only a select portion of each of the first leaflet 28, the second leaflet 30, the third leaflet 32 and the fourth leaflet 34 may flex radially away from the longitudinal axis 50 as a medical device passes therethrough. For example, only the portion of the first leaflet 28, the second leaflet 30, the third leaflet 32 and the fourth leaflet 34 which contacts a medical device passing through the introducer 10 may expand radially outward.

It can be appreciated from FIG. 3 and FIG. 5 that as the first leaflet 28, the second leaflet 30, the third leaflet 32 and the fourth leaflet 34 shift between an unexpanded configuration and an expanded configuration, the outer surfaces of the third leaflet 32 and the fourth leaflet 34 may contact and slide along the inner surfaces of the first leaflet 28 and/or the second leaflet 30. The ability of the leaflets to slide along one another is beneficial as it allows the leaflets to expand and adapt to the diameter of a medical device passing therethrough without necessarily having to expand to a maximum extent.

In some instances it may be desirable to control the maximum radially outward expansion of the first leaflet 28, the second leaflet 30, the third leaflet 32 and the fourth leaflet 34. As described above, FIG. 5 illustrates the projections 52 (extending radially inward from the inner surface 40 of the first leaflet 28 and the inner surface 42 of the second leaflet 30) engaged with the projections 54 (extending radially outward from the outer surface 48 of the third leaflet 32 and the outer surface 51 of the fourth leaflet 34). It can be appreciated that the engagement of the projections 52 with the projections 54 may limit the radial outward expansion of the first leaflet 28, the second leaflet 30, the third leaflet 32 and the fourth leaflet 34. While FIG. 5 illustrates the projections 52 and projections 54 being substantially rectangular in shape, in some examples the projections 52 and projections 54 may include shapes other than the rectangular shape shown. For example, the projections 52 and projections 54 may be rounded, curved, ovular, circular, triangular or any other shape which permits the projections to engage and limit the outward radial expansion of the leaflets.

Figure 6:
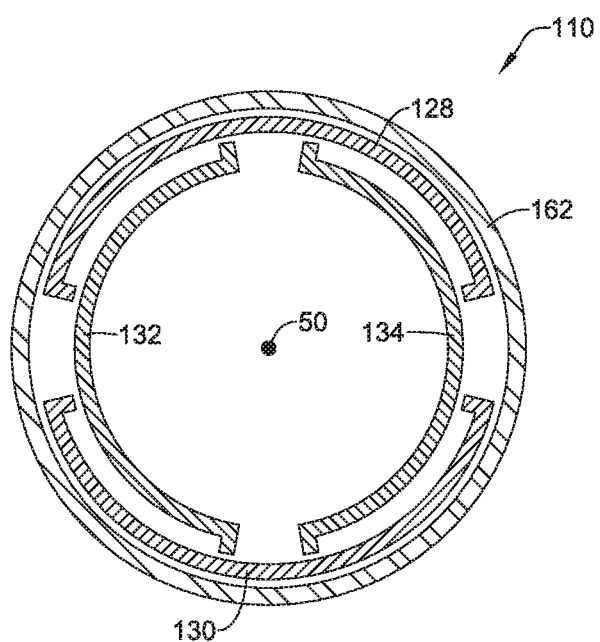
FIG. 6 is an end view of another example introducer.

FIG. 6 illustrates a cross-sectional view of another example introducer 110. The introducer 110 may be similar in form and function to the introducer 10 illustrated above. For example, the introducer 110 may include a first leaflet 128, a second leaflet 130, a third leaflet 132 and a fourth leaflet 134 spaced circumferentially around a longitudinal axis 50 of the introducer 110. Further, the first leaflet 128, the second leaflet 130, the third leaflet 132 and the fourth leaflet 134 may overlap and yet be circumferentially offset from one another around the longitudinal axis 50 of the introducer 110. Additionally, FIG. 6 illustrates that the introducer 110 may include an outer covering 162. The outer covering 162 may extent along either a portion or the entire length of the first leaflet 128, the second leaflet 130, the third leaflet 132 and the fourth leaflet 134.

It can be appreciated that the outer covering 162 may be a flexible covering designed to expand radially outward as the first leaflet 128, the second leaflet 130, the third leaflet 132 and the fourth leaflet 134 expand radially outward. In some examples, the covering 162 may be designed to limit the radial expansion of the first leaflet 128, the second leaflet 130, the third leaflet 132 and the fourth leaflet 134. In other words, the covering 162 may be designed to radially compress against the first leaflet 128, the second leaflet 130, the third leaflet 132 and the fourth leaflet 134, thereby limiting the radial expansion of the leaflets. The outer covering 162 may include an elastomeric material (e.g., elastomeric polymer material). Further, while FIG. 6 illustrates the outer covering 162 may be disposed along the introducer 110, it can be appreciated that the covering 162 may be included on any example introducer disclosed herein.

Figure 7:
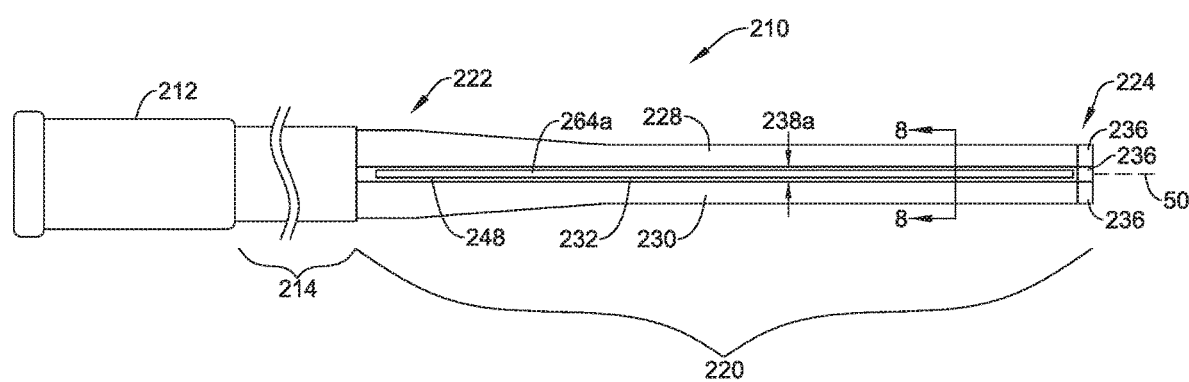
FIG. 7 is a side view of another example introducer.

FIG. 7 illustrates a side view of another example introducer 210. The introducer 210 may be similar in form and function to the introducer 10 illustrated above. For example, FIG. 7 shows a hub 212, a tubular member 214, an expandable portion 220 and a first leaflet 228, a second leaflet 230 and a third leaflet 232 (note that the fourth leaflet 234 extends from the proximal end region 222 to the distal end region 224, but is hidden from view in FIG. 7 by the third leaflet 232 extending from the distal end region 224 to proximal end region 222). Additionally, FIG. 7 shows the tip members 236 disposed along the distal ends of the first leaflet 228, the second leaflet 230 and the third leaflet 232. Additionally, FIG. 7 illustrates that the first leaflet 228 may be spaced away from the second leaflet 230 to define a first gap 238a between the first leaflet 228 and the second leaflet 230. It can be appreciated that the first gap 238a may extend along the longitudinal axis 50 from the distal end region 224 to the proximal end region 222 of the expandable portion 220.

Further, FIG. 7 illustrates that in some examples the introducer 210 may include a first rib member 264a disposed along the outer surface 248 of the third leaflet 232. It can be appreciated that the rib member 264a may improve (e.g., increase) the column strength of the third leaflet 232. The rib member 264a may extend longitudinally along the third leaflet 232 from the proximal end region 222 to the distal end region 224 of the expandable portion 220. Additionally, FIG. 7 illustrates that the rib member 264a may be positioned along the outer surface 248 such that it is spaced within the gap 238a.

Figure 8:
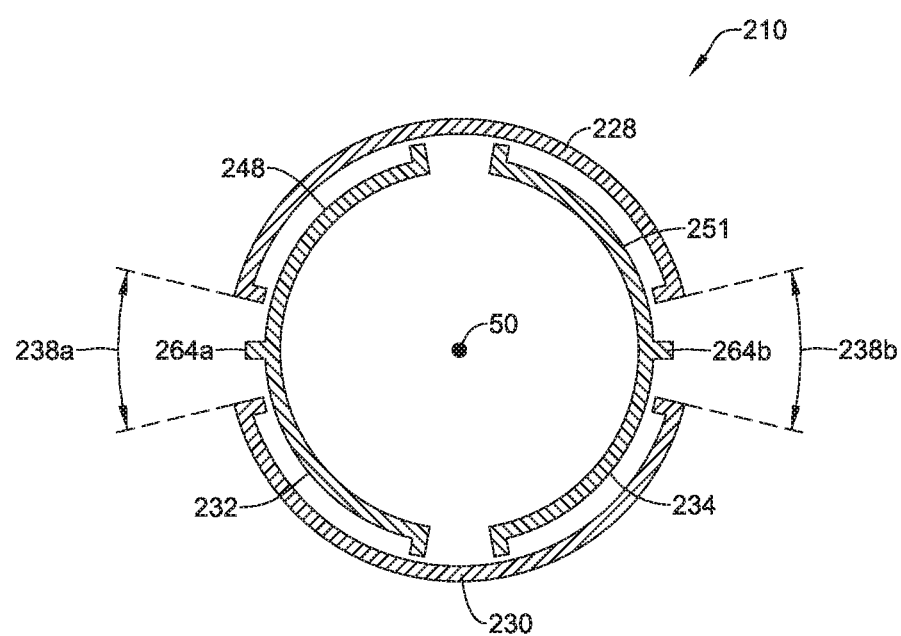
FIG. 8 is a cross-sectional view taken along line 8-8 of FIG. 7.

FIG. 8 illustrates a cross-sectional view taken along line 8-8 of FIG. 7. As discussed above, FIG. 8 illustrates the rib member 264a extending radially outward from the outer surface 248 of the third leaflet 232. As discussed above, FIG. 8 further illustrates that the rib member 264a is positioned on the outer surface 248 of the third leaflet 232 such that it lies within the gap 238a between the first leaflet 228 and the second leaflet 230.

Additionally, FIG. 8 illustrates that, in some examples, a second rib member 264b may be disposed along the outer surface 251 of the fourth leaflet 234. Similarly to that described above with respect to the rib member 264a, the rib member 264b may be positioned on the outer surface 251 of the fourth leaflet 234 such that it lies within a second gap 238b between the first leaflet 228 and the second leaflet 230. It can be appreciated that the rib member 264b may improve (e.g., increase) the column strength of the fourth leaflet 234.

Further, it is contemplated that the inner surface and/or outer surface of tubular member 14 or any of the leaflets defining the expendable member 20 may include one or more layers or coatings, such as a lubricious coating, a hydrophilic coating, a hydrophobic coating, or other suitable coatings, and the like, or may include a lubricant disposed thereon. Additionally, it is contemplated that in some examples contemplated herein, a liner may be disposed along the inner surface of tubular member 14 or any of the leaflets defining the expendable member 20. It is further contemplated that the liner may extend along the length of tubular member 14 or any of the leaflets defining the expendable member 20.

In some examples, the example introducers described herein may be disposed about or inserted over a guidewire (not shown), although the guidewire is not required. As discussed above, in some examples the hub and the tubular member of an example introducer may have an inner diameter or extent sufficient to accept a medical device passing therethrough, while the expandable portion of the introducer may have an inner diameter or radial extent in a relaxed condition that is less than a maximum outer diameter or extent of the medical device.

Figure 9:
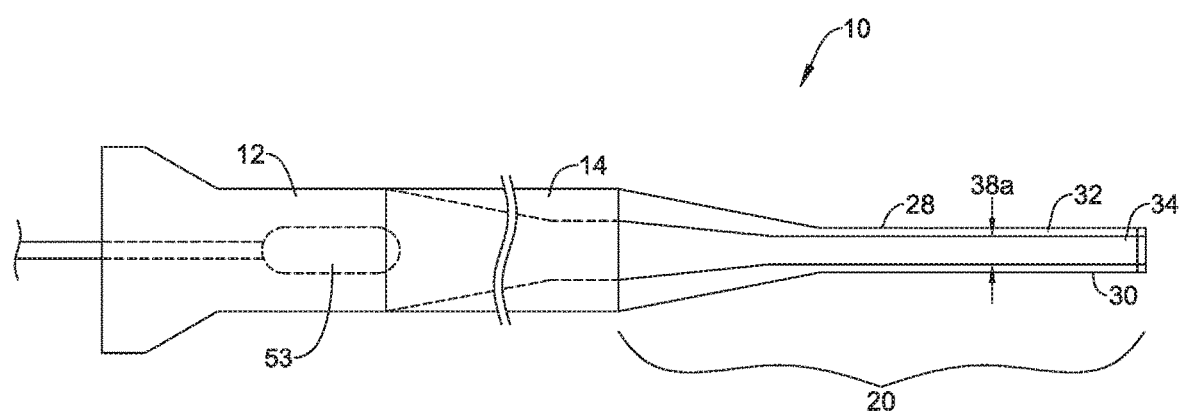
FIGS. 9-11 illustrate an example medical device being inserted through an example introducer.
Figure 10:
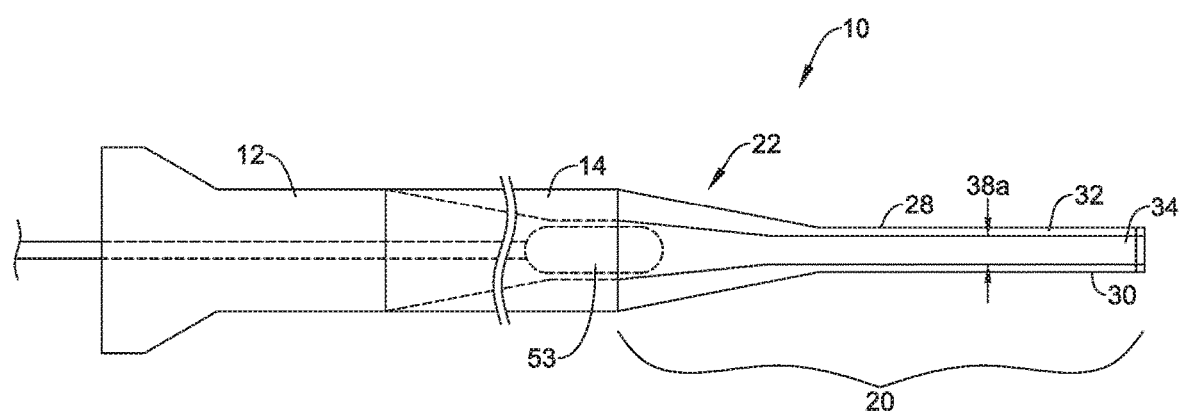
Figure 11:
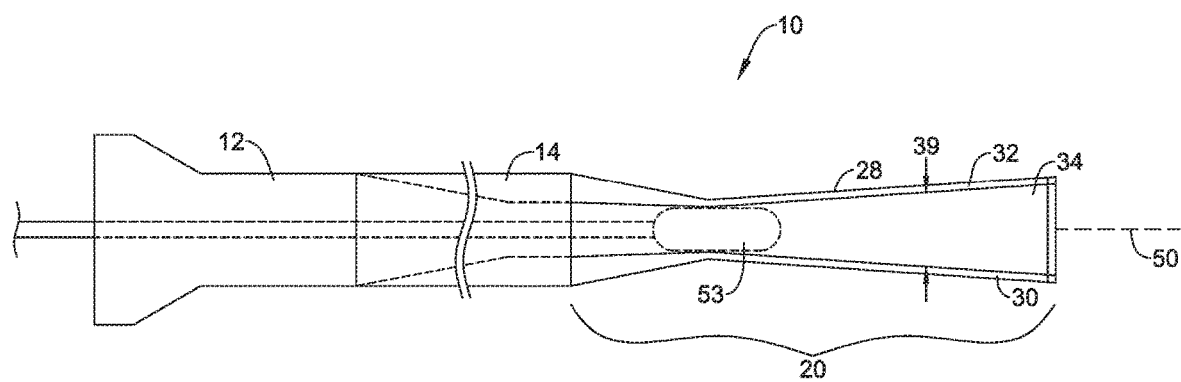

FIGS. 9-11 illustrate a method of use of introducer 10. While FIGS. 9-11 illustrate the use of the introducer 10, it can be appreciated that the methodology may apply to any of the example introducers disclosed herein.

FIG. 9 shows that an elongate medical device 53 (e.g., heart valve) may be inserted into a lumen (not shown for simplicity) of the introducer 10 and advanced distally toward the distal end of introducer 10. For example, the medical device may be advanced through the hub 12 and into the tubular member 14. It is noted that the first leaflet 28, the second leaflet 30, the third leaflet 32 and the fourth leaflet 34 (not shown is it is hidden by the first leaflet 28, second leaflet 30 and third leaflet 32) have not yet expanded in FIG. 9. As described above, FIG. 9 illustrates the unexpanded gap 38a between the first leaflet 28 and the second leaflet 30.

FIG. 10 illustrates that after passing through the tubular member 14, the medical device 53 may engage with the distal end region 22 of the expandable portion 20. It is noted that the first leaflet 28, the second leaflet 30, the third leaflet 32 and the fourth leaflet 34 (not shown is it is hidden by the first leaflet 28, second leaflet 30 and third leaflet 32) have not yet expanded in FIG. 10. As described above, FIG. 10 illustrates the unexpanded gap 38a between the first leaflet 28 and the second leaflet 30.

FIG. 11 illustrates that as the medical device 53 is advanced in a proximal-to-distal direction, the medical device 53 may exert a radially outward force on the inner surfaces of the first leaflet 28, the second leaflet 30, the third leaflet 32 and the fourth leaflet 34 (not shown is it is hidden by the first leaflet 28, second leaflet 30 and third leaflet 32). This radially outward force may cause the first leaflet 28, the second leaflet 30, the third leaflet 32 and the fourth leaflet 34 to flex radially away (e.g., radially outward) from the longitudinal axis 50 of the introducer 10 as the medical device 53 is advanced distally through the expandable portion 20. The radial expansion of the expandable portion 20 (including the first leaflet 28, the second leaflet 30, the third leaflet 32 and the fourth leaflet 34) from an unexpanded configuration to an expanded configuration illustrated in FIG. 11 may correspond to the expansion from an unexpanded to an expanded configuration of the first leaflet 28, the second leaflet 30, the third leaflet 32 and the fourth leaflet 34 illustrated and described above with respect to FIGS. 3-5 Accordingly, FIG. 11 illustrates the expanded gap 39 (described above with respect to FIG. 4) between the first leaflet 28 and the second leaflet 30.

Further, the expansion of the expandable portion 20 of the introducer 10 shown in above from an unexpanded configuration to an expanded configuration may be variable. For example, the diameter of the unexpanded expandable portion 20 of the introducer 10 may increase to an expanded diameter, after which, it may contract to a diameter that is greater than the diameter of the unexpanded configuration. However, this is not intended to be limiting. It is contemplated that once the unexpanded expandable portion 20 is expanded, it may remain expanded or it may return to any diameter less than the expanded diameter (including a diameter that is less than the unexpanded diameter).

In some examples, introducer 10 (or other example introducers and components thereof disclosed herein) may be made from materials such as metals, metal alloys, polymers, ceramics, metal-polymer composites, or other suitable materials, and the like. Some examples of suitable materials may include metallic materials such as stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymeric material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some examples, the introducer 10 (or other example introducers and components thereof disclosed herein) may be made from materials such as, for example, a polymeric material, a ceramic, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. In some examples, a suitable polymeric material may have a yield strain of at least 20%, at least 30%, at least 40%, at least 50%, or more. In some examples, the sheath, the membrane, and/or the plurality of corrugations may be made from a material having a low coefficient of friction. In some examples, the sheath, the membrane, and/or the plurality of corrugations may be formed from a fluoropolymer, such as polytetrafluoroethylene (PTFE) or fluorinated ethylene propylene (FEP).

Portions of introducer 10 (or other example introducers and components thereof disclosed herein) may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the elements described above (i.e., the sheath, the membrane, the medical device, etc.) may include or be formed from a radiopaque material. Suitable materials can include, but are not limited to, bismuth subcarbonate, iodine, gold, platinum, palladium, tantalum, tungsten or tungsten alloy, and the like.

It should be understood that although the above discussion was focused on percutaneous medical procedures within the vasculature of a patient, other examples or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the devices and methods described herein with respect to percutaneous deployment may be used in other types of surgical procedures as appropriate. For example, in some examples, the devices may be deployed in a non-percutaneous procedure. Devices and methods in accordance with the disclosure can also be adapted and configured for other uses within the anatomy.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. An introducer sheath, comprising:
a shaft including a tubular portion, an expandable portion coupled to the tubular portion and a longitudinal axis;
wherein the expandable portion includes a first pair of leaflets that includes a first leaflet and a second leaflet and a second pair of leaflets that includes a third leaflet and a fourth leaflet, and wherein both the first pair of leaflets and the second pair of leaflets extend along the longitudinal axis;
wherein the first leaflet includes a first concave surface that extends partially around the longitudinal axis, the second leaflet includes a second concave surface that extends partially around the longitudinal axis and the first concave surface faces the second concave surface;
wherein the third leaflet includes a third concave surface that extends partially around the longitudinal axis, the fourth leaflet includes a fourth concave surface that extends partially around the longitudinal axis and the third concave surface faces the fourth concave surface;
wherein the first leaflet and the second leaflet each include at least one radial projection that extends radially inward from a radially inward facing surface and the third leaflet and the fourth leaflet each include at least one radial projection that extends radially outward from a radially outward facing surface;
wherein the second pair of leaflets is spaced radially inward of the first pair of leaflets;
wherein the at least one radial projection of the first leaflet is configured to limit radial expansion of the expandable portion when engaged with the at least one radial projection of the third leaflet and the at least one radial projection of the second leaflet is configured to limit radial expansion of the expandable portion when engaged with the at least one radial projection of the fourth leaflet; and
wherein the expandable portion is designed to shift between a first radially compact configuration and a second radially expanded configuration.

2. The introducer of claim 1, wherein the first pair of leaflets are circumferentially offset from the second pair of leaflets.

3. The introducer of claim 1, wherein the first leaflet is spaced away from the second leaflet to form a first gap extending along the longitudinal axis and a second gap extending along the longitudinal axis.

4. The introducer of claim 3, wherein the third leaflet is spaced away from the fourth leaflet to form a third gap extending along the longitudinal axis and a fourth gap extending along the longitudinal axis.

5. The introducer of claim 1, wherein the first leaflet and the second leaflet are configured to flex radially outward and away from one another when the expandable portion shifts from the first radially compact configuration to the second radially expanded configuration.

6. The introducer of claim 5, wherein the third leaflet and the fourth leaflet are configured to flex radially outward and away from one another when the expandable portion shifts from the first radially compact configuration to the second radially expanded configuration.

7. The introducer of claim 1, wherein the first and second leaflets include an inner surface and wherein the third and fourth leaflets include an outer surface, and wherein the outer surface of the third and fourth leaflets are configured to slide along the inner surfaces of the first and second leaflets when the expandable portion shifts from the first radially compact configuration to the second radially expanded configuration.

8. The introducer of claim 3, wherein the third leaflet includes an outer surface and a first rib member disposed along the outer surface, and wherein the fourth leaflet includes an outer surface and a second rib member disposed along the outer surface.

9. The introducer of claim 8, wherein the first rib member is positioned within the first gap and wherein the second rib member is positioned within the second gap.

10. An introducer, comprising:
a hub; and
a shaft including a tubular member and an expandable portion coupled to a distal end region of the tubular member, and wherein a proximal end region of the tubular member is coupled to a distal portion of the hub;
wherein the tubular member has a constant outer diameter from the distal end region to the proximal end region;
wherein the expandable portion includes a first pair of leaflets and a second pair of leaflets spaced around a longitudinal axis of the expandable portion;
wherein the second pair of leaflets are spaced radially inward of an inner surface of the first pair of leaflets;
wherein each leaflet of the first pair of leaflets includes two longitudinal protrusions that extend along longitudinal edges of the leaflet and which extend radially inward from a concave inner surface thereof and each leaflet of the second pair of leaflets includes two longitudinal protrusions that extend along longitudinal edges of a leaflet and which extend radially outward from a radially outward facing surface of the leaflet; and
wherein the protrusions of the first pair of leaflets and the protrusions of the second pair of leaflets are configured to limit radial expansion of the expandable portion when a longitudinal protrusion of the first pair of leaflets contacts a longitudinal protrusion of the second pair of protrusions.

11. The introducer of claim 10, wherein the expandable portion is designed to shift between a first configuration and a second expanded configuration.

12. The introducer of claim 11, wherein the first pair of leaflets includes a first leaflet and a second leaflet, wherein the first leaflet includes a first concave surface extending around the longitudinal axis, where the second leaflet includes a second concave surface extending around the longitudinal axis and wherein the first concave surface faces the second concave surface.

13. The introducer of claim 12, wherein the second pair of leaflets includes a third leaflet and a fourth leaflet, wherein the third leaflet includes a third concave surface extending around the longitudinal axis, where the fourth leaflet includes a fourth concave surface extending around the longitudinal axis and wherein the third concave surface faces the fourth concave surface.

14. The introducer of claim 13, wherein the first pair of leaflets is circumferentially offset from the second pair of leaflets.

15. The introducer of claim 14, wherein the first leaflet, the second leaflet, the third leaflet and the fourth leaflet are configured to expand radially outward and away from one another when the expandable portion shifts from the first configuration to the second expanded configuration.

16. An introducer sheath, comprising:
a shaft including a tubular portion and an expandable portion coupled to the tubular portion;
wherein the expandable portion includes a first leaflet, a second leaflet, a third leaflet and a fourth leaflet spaced sequentially around a longitudinal axis of the expandable portion;
wherein the first leaflet, the second leaflet, the third leaflet and the fourth leaflet are radially and circumferentially offset from one another around the longitudinal axis;
wherein the first leaflet and the third leaflet are positioned radially outward from the second and fourth leaflets with the first leaflet overlapping the third and fourth leaflets and the second leaflet and overlapping the third and fourth leaflets;
wherein each leaflet includes two protrusions that extend along longitudinal edges of the leaflet with protrusions of the first and second leaflets that extend radially inward and protrusions of the third and fourth leaflets that extend radially outward;
wherein when the protrusions of a leaflet engage a protrusion of a circumferentially adjacent leaflet, the protrusions are configured to limit radial expansion of the expandable portion; and
wherein the expandable portion is designed to shift between a first configuration and a second expanded configuration.

17. The introducer of claim 1, wherein each the first, second, third, and fourth leaflets each include a second projection,
wherein the second radial projection of the first leaflet is configured to limit radial expansion of the expandable portion when engaged with second radial projection of the fourth leaflet and the second radial projection of the second leaflet is configured to limit radial expansion of the expandable portion when engaged with the second radial projection of the third leaflet.

\* \* \* \* \*